United States Patent
Maschke

(10) Patent No.: US 8,662,750 B2
(45) Date of Patent: Mar. 4, 2014

(54) MEDICAL EXAMINATION DEVICE FOR CT IMAGING AND FOR NUCLEAR MEDICAL IMAGING

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 292 days.

(21) Appl. No.: 13/105,036

(22) Filed: May 11, 2011

(65) Prior Publication Data

US 2011/0280364 A1    Nov. 17, 2011

(30) Foreign Application Priority Data

May 14, 2010  (DE) .......................... 10 2010 020 605

(51) Int. Cl.
*H05G 1/02*    (2006.01)

(52) U.S. Cl.
USPC ........................................................ 378/198

(58) Field of Classification Search
USPC ................ 378/4, 20, 193, 195, 196, 197, 198
See application file for complete search history.

(56) References Cited

U.S. PATENT DOCUMENTS

| | | | |
|---|---|---|---|
| 5,638,817 A | 6/1997 | Morgan et al. | |
| 6,661,866 B1 * | 12/2003 | Limkeman et al. | 378/19 |
| 6,940,941 B2 | 9/2005 | Gregerson et al. | |
| 7,695,192 B2 * | 4/2010 | Henderson et al. | 378/198 |
| 7,711,083 B2 * | 5/2010 | Heigl et al. | 378/20 |
| 2003/0014132 A1 | 1/2003 | Ohba et al. | |

FOREIGN PATENT DOCUMENTS

| | | |
|---|---|---|
| DE | 19839825 B1 | 10/1999 |
| DE | 10339493 A1 | 3/2004 |
| DE | 60223179 T2 | 8/2008 |
| DE | 102008019645 A1 | 10/2009 |

OTHER PUBLICATIONS

Siemens Medical Solutions, "Symbia True Point SPECT-CT", One exam. One workflow. Immeasurable versatility, 2004, pp. 1-15, Order No. A91004-M2330-M77-1-7600, Printed in Germany.
Siemens Medical Solutions, "Data: biograph family; Anyway you slice it, biograph gives you more" 2004, pp ,Order No. A91004-M2330-G029-7600, Printed in USA.
Medtronic Navigation, Inc., "O-arm® Multi-dimensional Surgical Imaging System, The Information You Need, When You Need It Most", Feb. 2011, pp. 1-22, 9670939 Rev 2.

* cited by examiner

Primary Examiner — Jurie Yun

(57) ABSTRACT

A medical examination device for CT imaging and for nuclear medical imaging is provided. The medical examination device has an essentially ring-shaped gantry with a CT imaging arrangement and a nuclear medical imaging arrangement. The gantry has an especially laterally arranged, fold-out or removable segment for creating an access opening to the interior of the gantry.

13 Claims, 8 Drawing Sheets

US 8,662,750 B2

MEDICAL EXAMINATION DEVICE FOR CT IMAGING AND FOR NUCLEAR MEDICAL IMAGING

CROSS REFERENCE TO RELATED APPLICATIONS

This application claims priority of German application No. 10 2010 020 605.9 filed May 14, 2010, which is incorporated by reference herein in its entirety.

FIELD OF THE INVENTION

The invention relates to a medical examination device for CT imaging and for nuclear medical imaging, especially for PET imaging or SPECT imaging, comprising a substantially ring-shaped gantry with a CT imaging arrangement and a nuclear medical imaging arrangement.

BACKGROUND OF THE INVENTION

In many cases of medical treatment, in the field of cancers for example, minimally-invasive interventions and minimal surgical interventions on a patient are increasingly replacing the classical surgical operations. A decisive factor in such cases is a good anatomical and functional medical imaging, especially of soft tissue. The previous mobile C-arm X-ray devices with fluoroscopy imaging are not sufficient for this, since these only deliver a two-dimensional image representation, no adequate soft tissue resolution and no functional medical imaging. It can also occur that the X-ray power is too weak to achieve a sufficiently good image quality with more complex interventions.

Computed tomography (CT) is an imaging technique which has long been known which offers outstanding image quality especially in relation to anatomy and soft tissue resolution. For better positioning of patients within a gantry, as disclosed in U.S. Pat. No. 6,940,941 B2 for example, a mobile CT gantry has been proposed in the CT field which can be opened up in order to better position the patient. However functional imaging is not possible with CT alone.

Nuclear medical imaging methods are especially suitable for functional imaging. Known examples of such methods are Positron Emission Tomography (PET) which is very well suited to functional diagnosis but delivers poor anatomical images. A typical PET system is described in US 2003/0014132. As part of a PET examination a radioactive tracer is injected into the patient. The tracer, for example FDG, collects explicitly in organs and/or tumors and allows a good diagnosis of the metabolism and thereby the discovery of tumors and metastases.

SPECT (Single Photon Emission Computer Tomography) related to PET also delivers functional imaging. A SPECT system is disclosed by U.S. Pat. No. 5,638,817 for example. A radioactive tracer is also injected into the patient in a SPECT examination. The tracer, for example 99 mTC-Methoxy-isobutylisonitrile, collects explicitly in organs and/or tumors and allows a good diagnosis of the metabolism and thereby the discovery of inflammations, tumors and/or metastases.

Since PET and SPECT deliver only poor anatomical imaging but CTE delivers good anatomical imaging, the use of a combination of a PET device or SPECT device with a CT device, frequently also referred to as PET/CT or SPECT/CT has become established. An integrated CT-PET system is described in DE 103 39 493 A1 for example.

The known hybrid systems are however not suitable for use in minimally-invasive interventions, since access to the patient is very restricted.

SUMMARY OF THE INVENTION

The underlying object of the invention is therefore to specify a medical examination device in which good access to a patient for carrying out a minimally-invasive intervention additionally offers the option of good anatomical and functional imaging.

To achieve this object, in a medical examination device of the type described at the outset, it is inventively proposed that the gantry features an especially laterally arranged, fold-out or removable segment to create an access opening to the interior of the gantry.

The starting point is thus an examination device which is suitable for CT imaging and for nuclear medical imaging, which provides a substantially ring-shaped gantry with a CT imaging arrangement and a nuclear medical imaging arrangement. The CT imaging arrangements are basically known. They comprise at least one radiation source and at least one radiation detector, with especially at least the radiation source, especially however also the radiation detector being arranged fully 360°-rotatably in the gantry in order to create CT projection images from different projections. The radiation source and the radiation detector are arranged in such cases opposite one another in the gantry. For example the radiation source and radiation detector can be arranged on a motorized rotor, with the gantry further able to include a rail system or other guidance system for guiding the rotor during rotation, which carries the radiation source and if necessary the detector.

The nuclear medical imaging arrangement can be a PET imaging arrangement or a SPECT imaging arrangement in this case. SPECT imaging arrangements can for example comprise two opposing detector units which are arranged on the gantry for rotation around an object to be recorded. Frequently this is PET detectors, which for example comprise a scintillator connected upstream of a collimator. A PET imaging arrangement usually comprises a ring of PET detectors arranged in the gantry which usually likewise comprise scintillators.

It is consequently possible, using the CT imaging arrangement and the nuclear medical imaging arrangement, to produce anatomical images with good soft tissue contrast and also functional images with a single examination device which, because of the known relation between the imaging arrangements, are registered with each other and can be processed jointly. The inventive examination device is however also especially advantageously suitable for use within the framework of a minimally-invasive intervention, since an especially laterally arranged segment of the gantry is able to be folded out or removed to provide an access opening to the interior of the gantry so that sufficient access to a patient is guaranteed in order to carry out a minimally-invasive interventions, for example the thermoablation of a tumor or the like.

Thus for example there can be provision for the patient initially, even with the gantry opened if necessary, to be positioned within the gantry so that an image of the intervention area can be captured by the imaging arrangement, i.e. lies within its field of view. Then, if necessary after closing the gantry, for which purpose suitable closure means can be provided, CT image data and nuclear medical image data can be captured in order to capture the intervention area before the intervention, for example to clearly show a tumor and its position. Then the gantry can be opened again so that an access to the patient is possible without the latter having to be repositioned. The intervention, for example the ablation of the tumor can be carried out, after which the gantry can be closed again and CT images and PET images can be recorded, which are able to be compared directly with the images captured before the intervention, which clearly show the successful progress of the treatment, especially both in respect of anatomical and also functional aspects. Finally a simpler removal of the patient from the gantry is also possible once the latter is opened again.

In this way a tool which is outstandingly suitable for interventional operations is made available with the inventive medical examination device, which improves the workflow for minimally-invasive interventions especially in respect of the generation of medical images which can profitably be analyzed.

In order to make possible a good access to the patient to allow an intervention, the segment can cover an angular range of 70-110°, especially 90°. Thus for example a quarter of the gantry can be folded out sideways or removed entirely so that sufficient access to the interior of the gantry is guaranteed.

To realize the ability to open the gantry in relation to the segment different possibilities are conceivable in accordance with the invention. There can thus preferably be provision for the segment to be able to be folded out by means of a hinge. Then as a result, especially at the lower edge of the segment, a hinge is provided by which the segment is coupled to the remainder of the gantry. If the segment is to be folded out, a suitable closure means at the other end of the segment can be released, so that it is easily possible to fold the segment out of the gantry in order to make access possible through the opening. In another embodiment the segment can be moved telescopically into the rest of the gantry, especially withdrawn into the latter. This can be done automatically by means of a suitable guide and suitable drive means. There can furthermore be provision in another embodiment for the segment to be able to be moved out of the gantry ring and to be displaced via guide means on the outside of the ring to form the opening. In this case the segment will be put into a park position, as it is when withdrawn telescopically, especially above the remaining part of the gantry, in order not to disrupt the usage of the opening.

In any event, as already mentioned, a closure device can be provided which retains the segment as a part of the gantry. Various closure devices are conceivable for this application, for example a closure arrangement can be provided that operates mechanically or magnetically. The precise embodiment of such different variants for the openability of the gantry are basically known to the person skilled in the art, for additional information the reader is referred to publication U.S. Pat. No. 6,940,941 B2 already mentioned at the start of this document, which hereby falls fully within the scope of the content disclosed by the present invention.

In another possible embodiment of an openable gantry there can also be provision for the segment to comprise the half of the gantry, especially the upper half which is able to be spaced by mechanical means away from the opposing half, especially the lower half, forming two opposing openings. One of the two openings formed is in this case the access opening allowing access to the patient.

While there can basically be provision for the gantry to be mounted fixed to the floor or to the ceiling of a room containing the gantry, especially advantageously there is provision for a mobile gantry to be used which can accordingly be driven, especially by means of rollers or a guide rail system. In this way a greater flexibility is achieved in the room in which the intervention is to be carried out by the gantry ultimately being able to be moved to any given position.

In a further advantageous embodiment there can be provision for the gantry to be supported in particular on a mount arranged on the ceiling, which allows at least one degree of freedom of movement for adjusting the gantry. Such a system, as already mentioned, can involve a rail system, which for example, when mounted on the ceiling of the room of a building, allows movement in one or two directions of the extent of the ceiling. Such guide rail systems are basically known. In especially expedient embodiment the gantry can be adjustable in three orthogonal spatial directions, for example an x-, a y- and a z-direction. To this end a height adjustment can be made possible for example in addition to the rail system already mentioned, for example by hydraulic or pneumatic means. It should be pointed out however that the mount can naturally also include articulated joints which make it possible to tilt or rotate the gantry.

In an especially advantageous embodiment the stand can comprise an articulated-arm robot, especially an articulated-arm robot with at least four, preferably with at least six degrees of freedom. In this way the gantry can ultimately be moved freely in the room, in which case once again a ceiling-mounted articulated-arm robot in particular is suitable as a part of the mount. It is precisely the facilitation of six degrees of freedom of movement that provides the greatest possible flexibility in the positioning of the gantry.

The examination device can further comprise a patient support means, especially a patient table. This patient support means can also especially advantageously exhibit at least one degree of freedom of movement for automatic and/or manual adjustment, so that a number of further degrees of freedom for relative positioning of the patient and of the gantry are provided in this way, facilitating further simplification of the positioning and further flexibility. In such cases there can especially be provision for the patient table to be adjustable in at least two spatial directions orthogonal to each other and/or along at least one orbital or elliptical track and/or to be able to be tilted or rotated around at least one axis. It should further be noted that the patient support means can also the floor-mounted, wall or ceiling-mounted, but that basically a mobile patient support means is preferred.

As already mentioned, various embodiments of the degrees of freedom of movement of the patient support means are conceivable. Thus there can be provision for example for the height and/or length and/or transverse direction of the patient table to be adjusted manually or by motor. Furthermore there can be provision for the patient table to be tilted in at least one direction, especially in all three spatial directions. In a further embodiment the patient table can be additionally or as an alternative be rotated around a central point. Orbital or elliptical rotation movements around a fixed point in the plane or the room can also be provided. It is clear that a very wide diversity of embodiments is conceivable in order to make the appropriate degrees of freedom of movement possible.

A hydraulic drive device and/or a pneumatic drive device and/or an electrical drive device can be provided as at least one mechanical drive device for adjusting the gantry and/or the patient support means. Here too basically all drive devices known to the person skilled in the art can be advantageously employed in order to obtain the different degrees of freedom of movement of the gantry and/or the patient support means.

BRIEF DESCRIPTION OF THE DRAWINGS

Further advantages and details of the present invention emerge from the exemplary embodiments described below as well as with reference to the drawings, in which.

DETAILED DESCRIPTION OF THE INVENTION

It should be pointed out in advance that although the exemplary embodiments depicted here all show a PET recording arrangement as a nuclear medical recording arrangement, all the exemplary embodiments can naturally also be provided with an SPECT recording arrangement.

Figure 1:
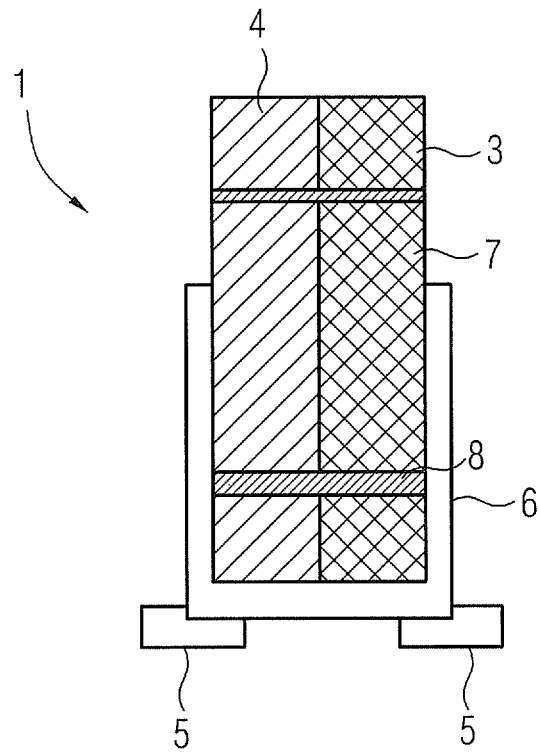
FIG. 1 shows a side view of a gantry in a first foam of embodiment of an inventive examination device.
Figure 2:
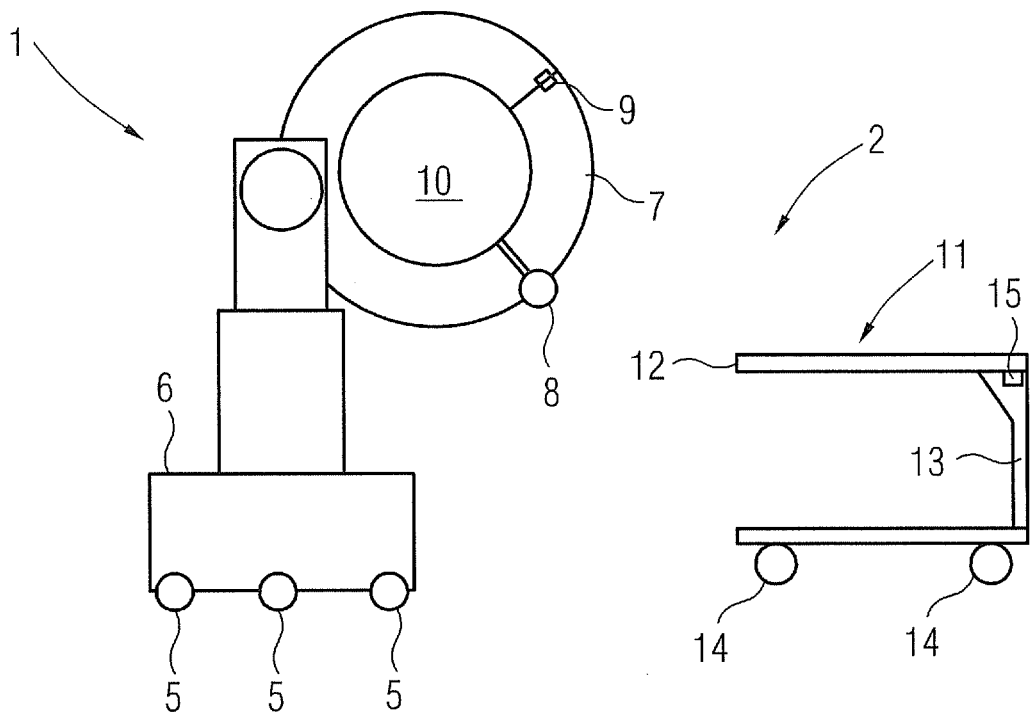
FIG. 2 shows a view of the first form of embodiment of the inventive examination device.

FIG. 1 shows the gantry 1 of a first embodiment of an inventive examination device 2 (FIG. 2). The gantry 1 comprises a CT recording arrangement 3 and a PET recording arrangement 4, as are basically known and do not need to be explained in greater detail here. It is basically embodied in the form of a ring, cf. FIG. 2 and is supported on a mount 6 able to be moved in this case by means of rollers 5. The internal diameter of the gantry can amount to 60 cm or 70 cm for example.

The gantry 1 with the two recording arrangements is now characterized by the fact that it includes a fold-out segment 7 which encloses the side facing away from the mount 6 by 90° and is arranged on a hinge 8 on the lower end of the rest of the gantry 1. Provided on the upper side is a closure device 9, here a controllable closure device, in order to keep the gantry 1 in a closed position. If the closure device 9 is opened, the segment 7 can be folded out and reveals an access opening to the interior 10 of the gantry.

It should also be pointed out at this juncture that in the forms of embodiment depicted here, a segment 7 is described which is basically able to be folded out via a hinge 8. Naturally the openability of the gantry can however be achieved in other ways, for example by moving the segment 7 out and by guide means, so that the segment 7 can be moved into a park position above the gantry 1. A telescopic receptacle for the segment 7 in the other part of the gantry also falls within the framework of the present invention, as does a complete removal of the segment 7 which can be inserted again later. Finally the reader is also referred to an embodiment in which the segment 7 comprises the upper half of the gantry 1 which can be spaced via mechanical means away from the lower half of the gantry 1 in order to form opposing openings. To conclude, a few of these embodiments will be shown in greater detail.

The examination device 2 further comprises a patient support means 11, here a patient table 12. This has a support foot 13 on its edge in order in this way to position all areas of the patient or of a part of the patient in the interior 10 of the gantry 1 if possible. The patient table 12 is further supplied with rollers 14, meaning that it is also mobile.

The patient table 12 comprises different drive devices, only indicated by the reference number 15, for automatic user controlled adjustment of the patient table 12, which can be moved for example in the longitudinal direction and transverse direction and is also height-adjustable. In addition the patient table 12 can be tilted and can be rotated around at least one point in the room. Embodiments are also conceivable in which the patient table is embodied to describe an orbit or elliptical track during adjustment. Thus the patient table 12 through the drive devices 15 already offers great flexibility in positioning a patient. It should however be pointed out that some adjustment options can also be realized manually.

Figure 3:
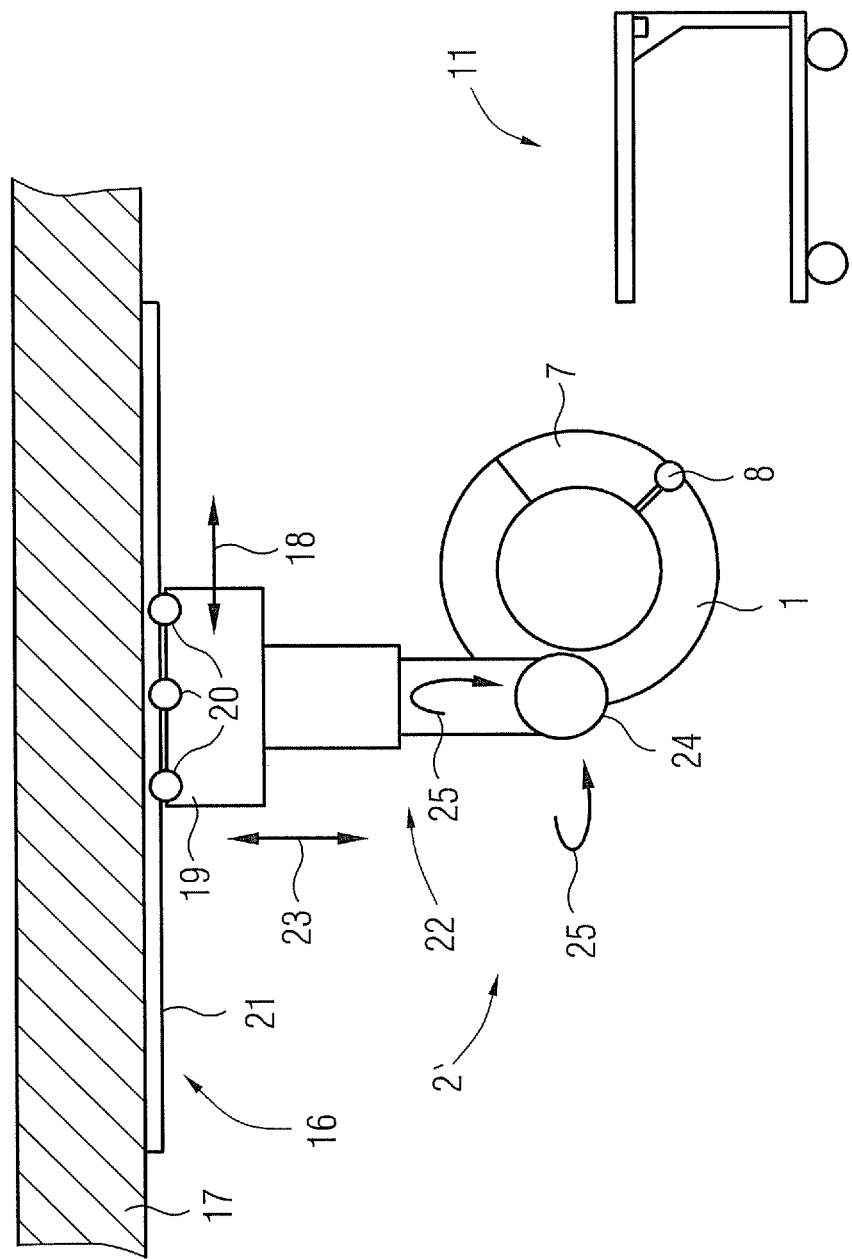
FIG. 3 shows a second form of embodiment of an inventive examination device.

FIG. 3 shows a second form of embodiment of an inventive examination device 2' which in this case is supported movably via rail system 16 on a ceiling 17. Thus the movement in the directional arrow 18 is possible, with additionally a movement in a direction extending at right angles to the direction 18 of the ceiling 17 able to be made possible. In the present case a ceiling mount 19 supporting the gantry 1 is guided by rollers 20 in at least one ceiling rail 21.

The gantry 1 (for simplification matching reference characters are used in the diagram for matching components) again features the CT recording arrangement 3 not shown in any greater detail here and the PET recording arrangement 4 and again comprises a segment 7 which is supported to enable it to be folded out via the hinge 8. A locking device 9 is also present, but for reasons of improved clarity is no longer shown in detail in this embodiment nor in the following exemplary embodiments.

The mount 19 further comprises a hydraulic drive device 22 to make it possible to adjust the height of the gantry 1, cf. arrow 23. The gantry is given further adjustment options/degrees of freedom of movement by an articulated joint 24 which allows rotations in accordance with the arrows 25.

The patient support means 11 of the examination device 2' corresponds to the patient support means 11 of the examination device 2 and will thus not be explained here in any greater detail.

Figure 4:
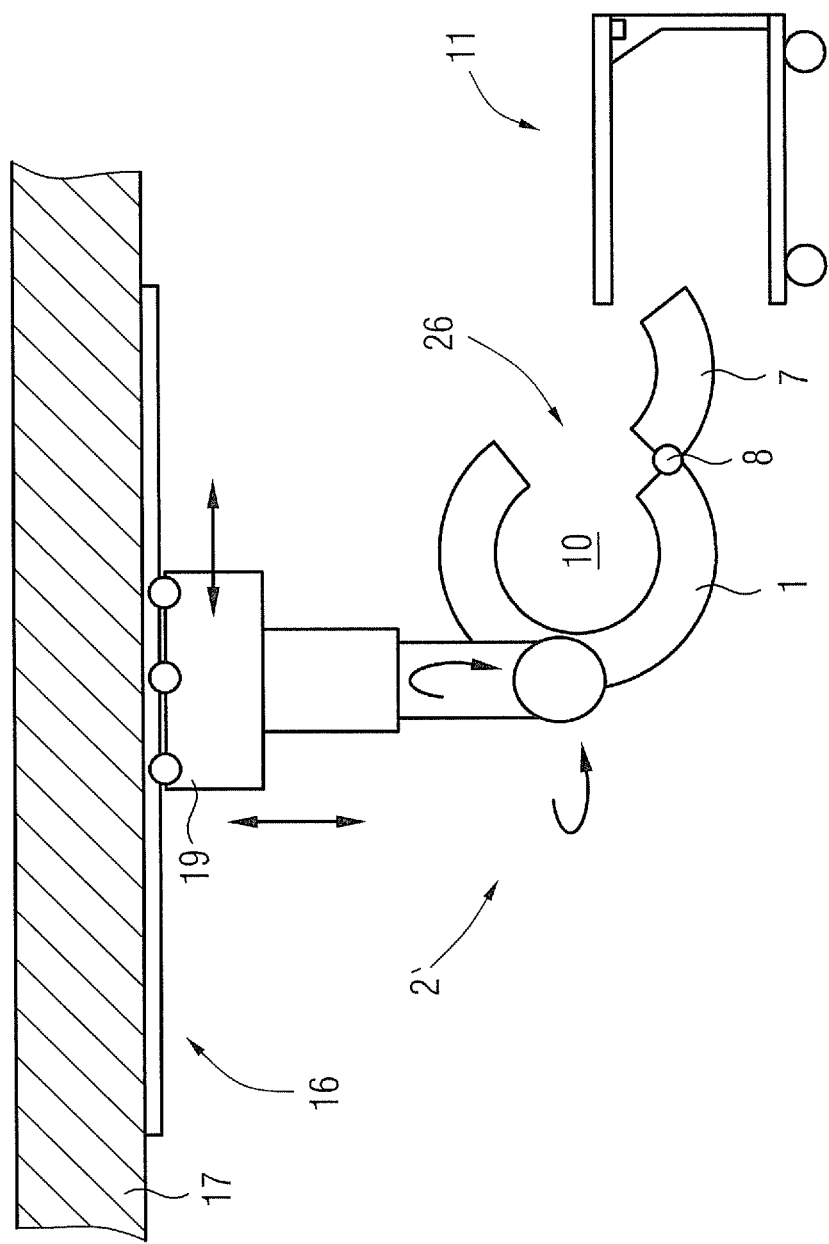
FIG. 4 shows the second form of embodiment of the inventive examination device with the gantry folded out.

FIG. 4 shows the second form of embodiment of the examination device 2' with the gantry 1 open, meaning that segment 7 is folded out, so that an access opening 26 to the interior 10 of the gantry 1 is produced, so that a minimally-invasive intervention can be carried out when a patient is positioned within the gantry 1.

Figure 5:
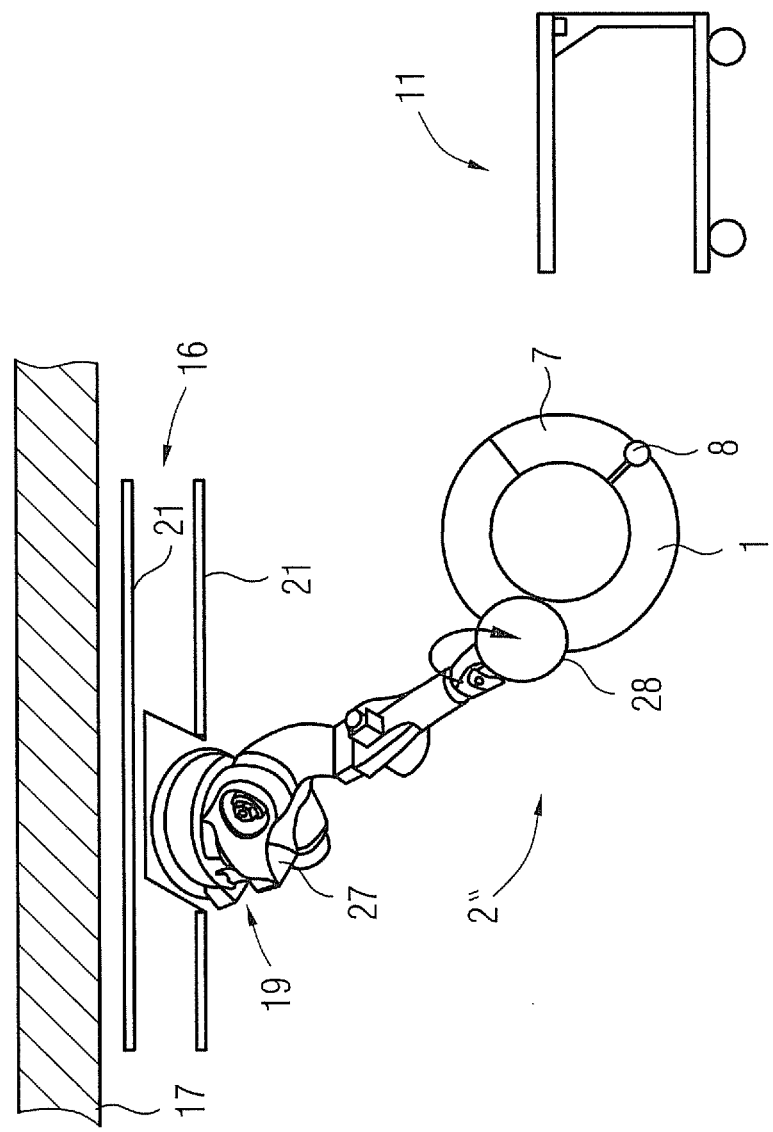
FIG. 5 shows a third form of embodiment of an inventive examination device.

FIG. 5 shows a third form of embodiment of an inventive medical examination device 2". This differs from the form of embodiment shown in FIGS. 3 and 4 in that the mount here comprises an articulated-arm robot 27 with six degrees of freedom on which the gantry 1 is supported via an articulated joint 28. Since a rail system 16 with ceiling rails 21 is likewise also present, in this form of embodiment an especially great flexibility in relation to the positioning of a patient is provided, since both the gantry 1 is able to be moved relatively freely in the room and the patient support means 11 embodied as in the first form of embodiment likewise exhibits a plurality of degrees of freedom of movement.

Figure 6:
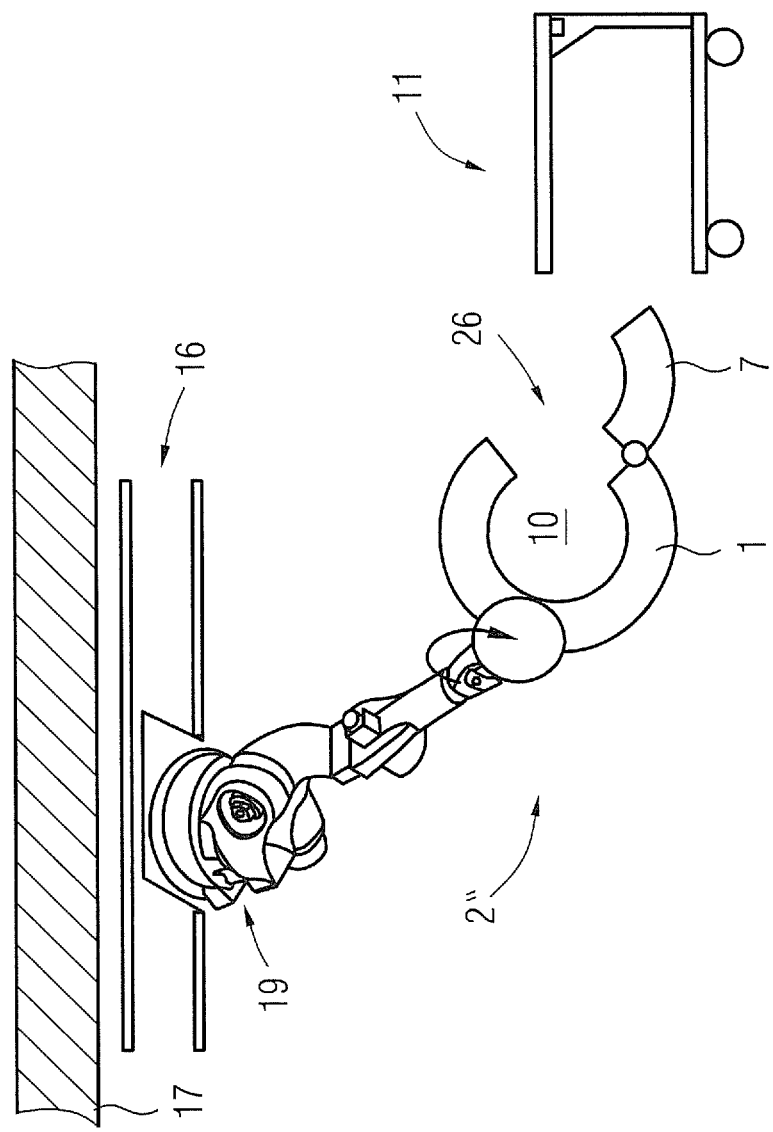
FIG. 6 shows the third form of embodiment of the inventive examination device with the gantry folded out.

FIG. 6 shows the examination device 2" once more, with the segment 7 of the gantry 1 folded out, so that here too an access opening 26 to the interior 10 of the gantry 1 is produced. Naturally the gantry 1 of the examination device 2" also comprises a PET recording arrangement 4 and a CT recording arrangement 3.

Figure 7:
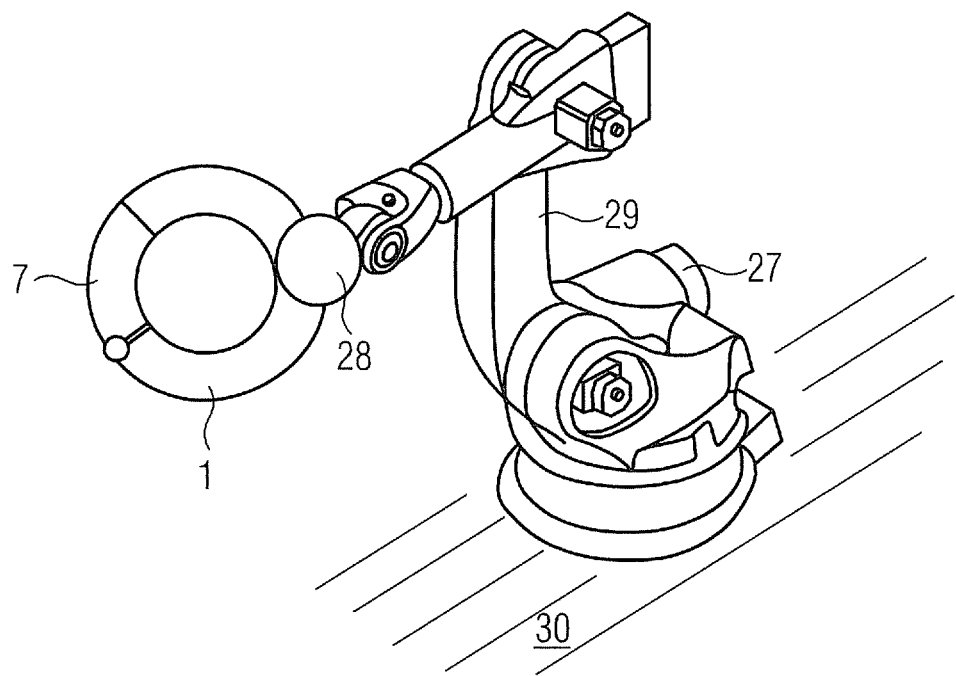
FIG. 7 shows a fourth form of embodiment of an inventive examination device.

FIG. 7 shows the gantry 1 with associated mount 29 in a fourth form of embodiment of an inventive examination device. The mount 29 again comprises an articulated-arm robot 27 and a swivel joint 28, but in this case is mounted in a fixed position on the floor 30 of a room.

Figure 8:
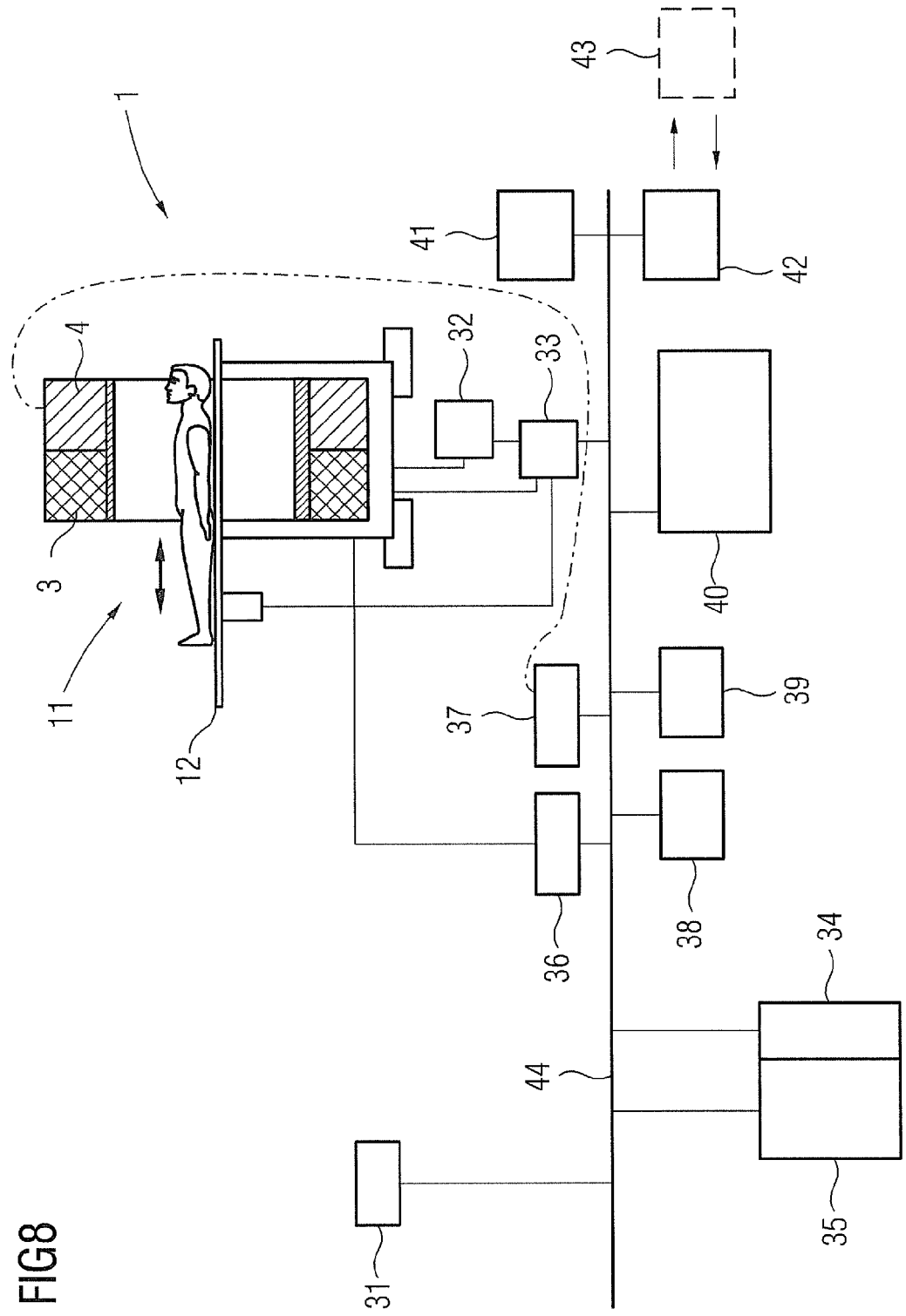
FIG. 8 shows a basic diagram of other system components of the inventive examination device.

FIG. 8 shows a diagram of further components present in the inventive examination devices 2, 2', 2" presented as well as the fourth form of embodiment which is able to be employed as a basic sketch for all the exemplary embodiments previously shown.

Shown schematically are the patient support means 11, i.e. the patient table 12, as well as the gantry 1 with the CT recording arrangement 3 and the PET recording arrangement 4 which naturally, as already mentioned, can also be replaced by an SPECT recording arrangement.

A power supply unit 31 handles the power supply for the examination device while a high-voltage generator 32 is present for generating a high voltage for the least one radiation source of the CT recording arrangement 3. Central control is handled by a control device 33, which also drives corresponding drive devices 15 of the patient support means 11 and the different drive devices of the gantry 1. Furthermore the operation of the recording devices 3, 4 and also the opening of the segment 7, where this is able to be controlled, is controlled by the control device 33.

For entry of data, recording parameters and also control commands for drive devices and the like, an operating device 34 and a display device 35, for example a monitor, is also provided, which is embodied for displaying recorded images.

Further components of the system architecture are preprocessing units 36 and 37 for the CT images and the PET images respectively as well of corresponding image processing units 38, 39. An image fusion unit 40, which can also be embodied for segmentation, registration and reconstruction, is present as is an image data memory 41 for the image data. Data can typically be exchanged with a hospital information system indicated by the number 43 via a Dicom interface 42 for patient data and image data. A data bus 44 is also provided for communication between the individual components.

FIGS. 9-12 now show further embodiments for the openability of the gantry as basic diagrams.

Figure 9:
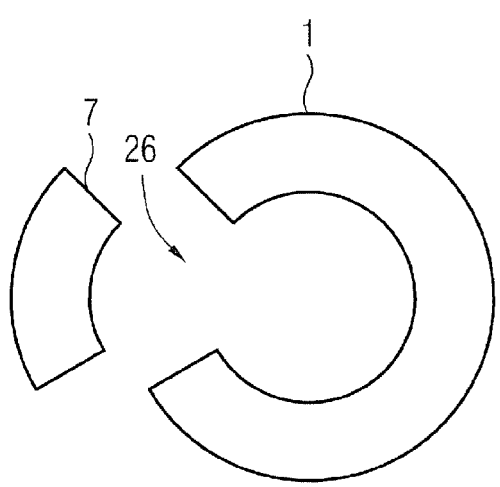
FIG. 9 shows a basic diagram for a second embodiment of the openability of the gantry.

Thus FIG. 9 shows a segment 7 of the gantry 1 that can be completely removed in order to create the access opening 26.

Figure 10:
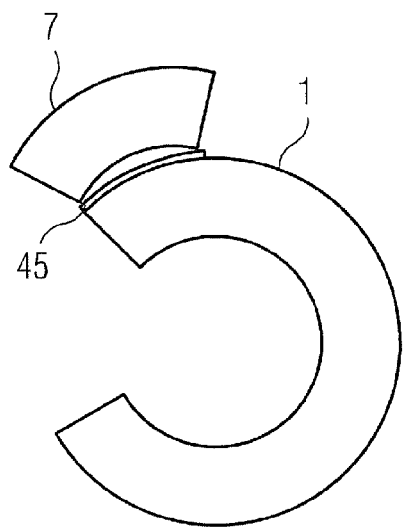
FIG. 10 shows a basic diagram for a third embodiment of the openability of the gantry.

In FIG. 10 the segment 7 is able to be moved out of the gantry 1 and brought by means of guide means 45 into a park position lying above the gantry 1.

Figure 11:
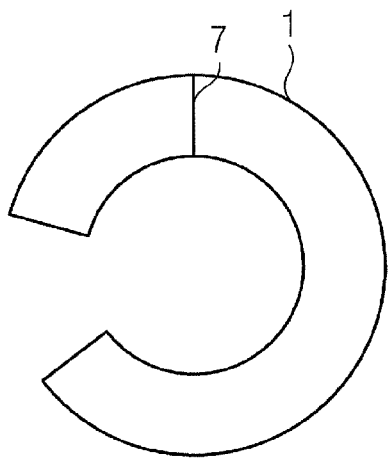
FIG. 11 shows a basic diagram for a fourth embodiment of the openability of the gantry.

FIG. 11 shows how the segment 7 can be retracted telescopically within the rest of the gantry by being moved into the latter.

Figure 12:
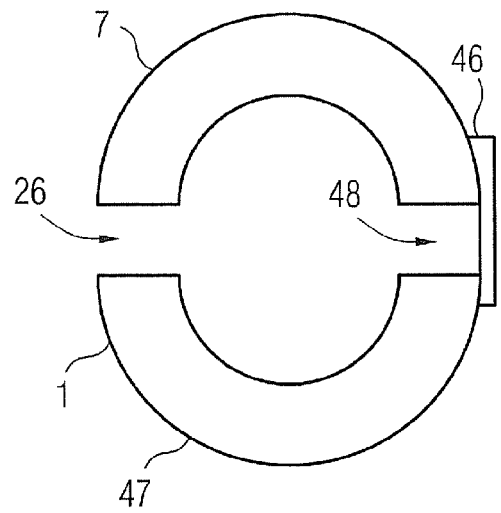
FIG. 12 shows a basic diagram for a fifth embodiment of the openability of the gantry.

FIG. 12 finally shows an example in which the segment 7 comprises the upper half of the gantry 1. It is now possible via mechanical means 46 to space the segment 7 away from the lower half 47 of the gantry 1 so that the access opening 26 is produced along with a further opening 48, of which no further use is made here.

The invention claimed is:

1. A medical examination device for CT imaging and for nuclear medical imaging, comprising:
   a annular gantry comprising an laterally arranged segment to create an access opening to an interior of the gantry;
   a CT imaging arrangement and a nuclear medical imaging arrangement arranged on the gantry;
   a patient support table;
   a control device for controlling operation of the CT imaging arrangement and the nuclear medical imaging arrangement and drive devices for adjusting the gantry and the patient support table; and
   a mount for supporting the gantry,
   wherein the mount is mounted on a ceiling and is able to be moved by a guide rail.

2. The examination device as claimed in claim 1, wherein the nuclear medical imaging arrangement is a PET imaging arrangement or a SPECT imaging arrangement.

3. The examination device as claimed in claim 1, wherein the segment encloses an angular area of 70° to 110°.

4. The examination device as claimed in claim 3, wherein the segment encloses an angular area of 90°.

5. The examination device as claimed in claim 1, wherein the segment is folded out by a hinge.

6. The examination device as claimed in claim 1, wherein the segment is completely moved out of the gantry, or is telescopically moved into a remainder of the gantry, or is moved into a park position above the gantry to create the access opening.

7. The examination device as claimed in claim 1, wherein the segment comprises half of the gantry that is spaced by a mechanical device away from an opposing half of the gantry to create two opposite openings.

8. The examination device as claimed in claim 1, wherein the mount comprises an articulated-arm robot with at least four degrees of freedom.

9. The examination device as claimed in claim 8, wherein the articulated-arm robot has six degrees of freedom.

10. The examination device as claimed in claim 1, wherein the gantry is able to be adjusted in three orthogonal spatial directions.

11. The examination device as claimed in claim 1, wherein the patient support table has at least one degree of freedom of movement for automatic and/or manual adjustment.

12. The examination device as claimed in claim 1, wherein the patient support table is able to be tilted or rotated around at least one axis in at least two spatial directions orthogonal to one another and/or along at least one orbital or elliptical track.

13. The examination device as claimed in claim 1, wherein the drive devices comprise a hydraulic drive device and/or a pneumatic drive device and/or an electric drive device.

* * * * *